April 26, 1966 R. G. JELLY Plant Pat. 2,624
ROSE PLANT
Filed Jan. 26, 1965
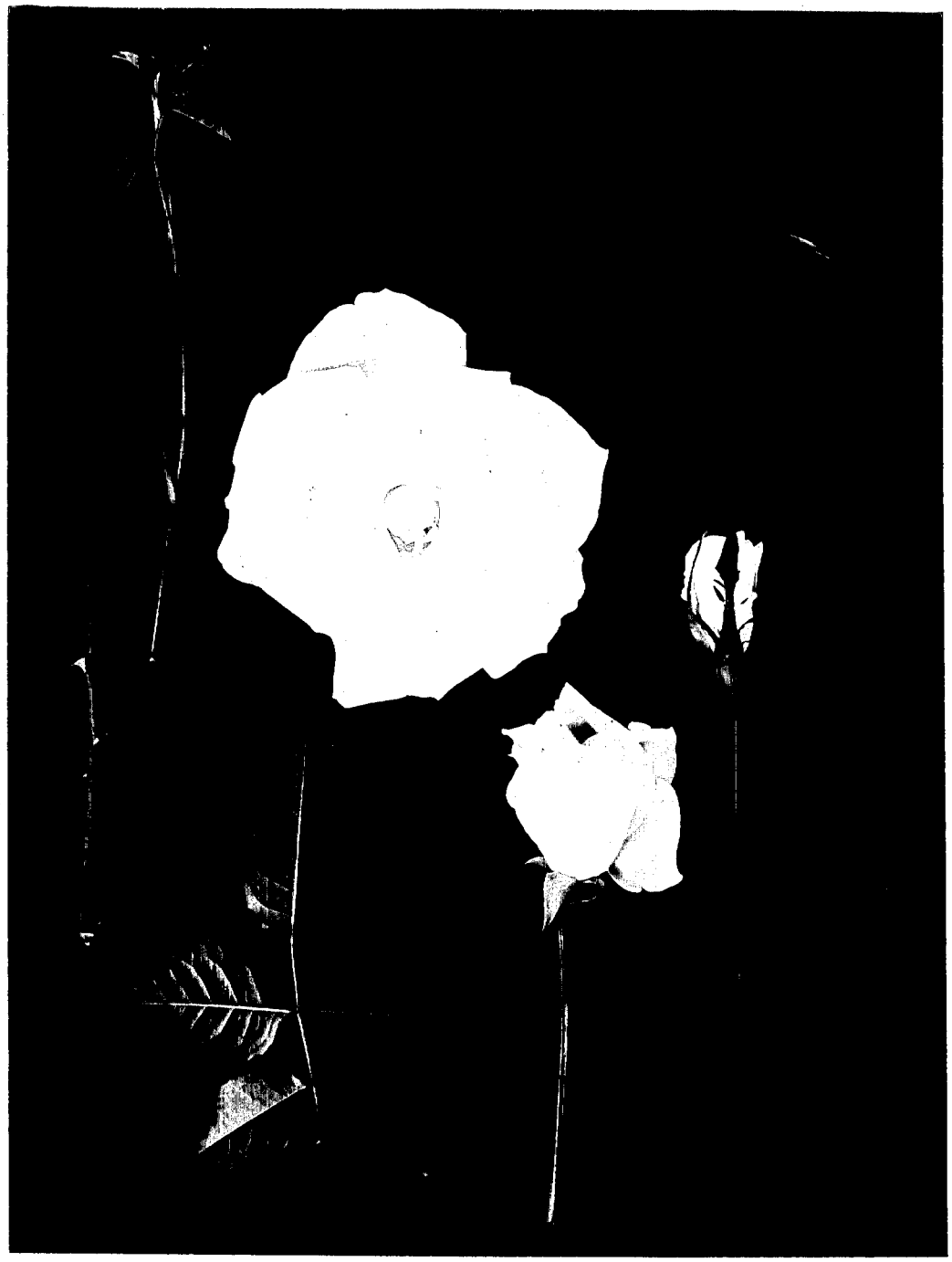
Inventor.
Robert G. Jelly
By: Dodd & Cobb
Attorneys.

United States Patent Office

Plant Pat. 2,624
Patented Apr. 26, 1966

2,624
ROSE PLANT

Robert G. Jelly, Richmond, Ind., assignor to E. G. Hill Co., Inc., Richmond, Ind., a corporation of Indiana Filed Jan. 26, 1965, Ser. No. 428,278
1 Claim. (Cl. Plt.—14)

The present invention relates to a new and distinct variety of rose plant of the hybrid tea class, which was originated by me by crossing the variety "Snowsong" (Plant Patent No. 2,165) with the variety "White Butterfly" (Plant Patent No. 1,337).

The primary objective of this breeding was to produce a new rose variety which eliminates some of the problems which occur in producing and marketing the two parent varieties, and to develop a new white rose that would give improved customer satisfaction as cut flowers. This objective was fully achieved along with other desirable improvements, as evidenced by the following unique combination of characteristics which are outstanding in the new variety and which distinguish it from its parents, as well as from all other varieties of which I am aware:

(1) A vigorous habit of growth;
(2) Excellent flower productivity;
(3) Distinctive and attractive white flowers of classic form which open from pointed buds;
(4) Good color retention throughout the year when grown in greenhouses; and
(5) Good tolerance to insecticides.

In comparison with its seed parent, "Snowsong," the white flower color of the new variety is maintained more consistently throughout the year, the flowers have a much nicer concentric opening form, and the plants exhibit a higher degree of vigor.

As compared with its pollen parent, "White Butterfly," the new variety exhibits a much higher degree of tolerance to insecticides, while having some of the growth characteristics, as well as the excellent white flower color, of this parent.

Asexual production of the new variety by grafting, as performed at Richmond, Indiana, and also by budding, as performed at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in color illustration of this character.

The following is a detailed description of the new variety, with color terminology in accordance with Robert S. Wilson's Horticultural Colour Chart (hereinafter abbreviated as (W)), and Nickerson Color Fan (hereinafter abbreviated as (N)), as indicated, except where general color terms of ordinary dictionary significance are obvious:

Type: Seedling; greenhouse; for cut flowers.
Class: Hybrid tea.
Breeding: Seedling.
*Seed parent.*—"Snowsong."
*Pollen parent.*—"White Butterfly."
Propagation: Holds its distiguishing characteristics through succeeding propagations by both grafting and budding.

*Flower*

Locality where grown and where following observations were made: Richmond, Indiana.
Flowers borne: Usually singly, but sometimes producing three buds to stem during periods of extremely vigorous growth and which are usually disbudded commercially to a single bud for the production of cut flowers; on stems of medium length and medium strength.
Quantity of bloom: Abundant, in greenhouse.
Continuity: Continuous, in greenhouse.
Fragrance: Moderate, in greenhouse.
*Nature.*—Sweetbriar.
Bud:
*Peduncle.*—Medium length; medium diameter; erect; medium strong. Bark—smooth. Color—shaded from Lettuce Green, Plate 861 (W) to slightly darker than Lettuce Green, Plate 861 (W). Thorns — none. Prickles — none. Hairs—none.
*Before calyx breaks.*—Size—medium. Form—long pointed; with a conspicuous neck; with foliaceous appendages on the surface of the bud; with slender foliaceous parts extending beyond the tip of the bud to ¼ or more of its length. Color—shaded from Scheeles Green, Plate 860/2 (W) at base to Moderate Yellow Green, Plate 5GY5/6 (N) at tip.
*As calyx breaks.*—Color—outside petal Sap Green, Plate 62/3 (W) with venation Sap Green, Plate 62/2 (W).
*As first petal opens.*—Size—medium large. Form—long pointed. Color—outside—white, with venation shaded from Brilliant Yellow Green, Plate 2.5GY9/8 (N) to Brilliant Yellow Green, Plate 2.5GY8/9 (N); inside — white, with venation shaded from Sap Green, Plate 62/3 (W) to Sap Green, Plate 62/2 (W) at base.
*Opening.*—Opens up well in greenhouse; bud size decreases with prolonged periods of hot weather.
Bloom:
*Size (when fully open).*—Medium large; from 4½ inches to 5¼ inches.
*Petalage.*—Double; from 20 to 25 petals; arranged regularly.
*Form.*—High-centered at first and remaining high-centered; petals being at first tightly rolled inward, but later becoming loosely rolled outward at maturity.
Petals:
*Texture.*—Moderately thick.
*Appearance.*—Inside—shiny and satiny; outside—only slightly satiny.
*Shape.*—Outer—from oval to ovate, with occasional scalloping, and with variable apex, some cuspidate and some having from one to several notches. Intermediate—from oval to slightly ovate, with apex slightly cuspidate. Inner—from oval to slightly ovate, with apex slightly cuspidate.

This description of a newly opened flower was made from a rose grown in a greenhouse during the month of March at Richmond, Indiana:

*Color.*—Outer petal—outside surface—white, with petal base and venation at base shaded from Uranium Green, Plate 63/3 (W) to Uranium Green, Plate 63/2 (W); inside surface—white, with petal base and base venation Sap Green, Plate 62/2 (W). Intermediate petal—outside surface—white, with petal base and base venation shaded from Chartreuse Green, Plate 663/3 (W) to Chartreuse Green Plate 663/2 (W); inside surface—white, with venation at petal base Chartreuse Green, Plate 663/2 (W). Inner petal—outside surface—white, with basal venation shaded from Chartreuse Green, Plate 663/3 (W) to Chartreuse Green, Plate 663/2 (W); inside surface—white, with basal venation shaded from Chartreuse Green, Plate 663/3 (W); to Chartreuse Green, Plate 663/2 (W).

This description was made from a rose that was open for three days in a greenhouse during the month of March at Richmond, Indiana:

*Color.*—Outer petal—outside surface—white, with a slight trace of Sulphur Yellow, Plate 1/3 (W) at base; inside surface—white, with Sulphur Yellow, Plate 1/2 (W) at base. Intermediate petal—outside surface—white, with a slight trace of Sulphur Yellow, Plate 1/3 (W) at base; inside surface—white, with Sulphur Yellow, Plate 1/2 (W) at base. Inner petal—outside surface—white, with a slight trace of Sulphur Yellow, Plate 1/3 (W) at base; inside surface—white, with Sulphur Yellow, Plate 1/2 (W) at base.

*General color effect.*—Newly opened flower—white, with a slight cast of Chartreuse Green, Plate 663/3 (W) on lower portion of petals surrounding stamens. 3-days open—white, with a slight cast of Sulphur Yellow, Plate 1/3 (W) on lower portion of petals surrounding stamens.

*Behavior.*—Drop off cleanly; slight decrease in petal number and size during hot weather, but remaining white in color until decay sets in.

*Flower longevity.*—Cut roses in greenhouse and kept at living room temperatures—6 days in March.

*Plant*

Foliage:

*Leaves.*—Compound of usually 3 to 5 but occasionally 7 leaflets; normal abundance; medium size; moderately thin.

*Leaflets.*—Shape—from oval to slightly cordate. Apex—cuspidate. Base—from obtuse to slightly cordate. Margin—serrate.

*Color.*—Mature—upper surface—Ivy Green, Plate 0001060/2 (W); under surface—a shade lighter than Leek Green, Plate 000858 (W) but greener than Leek Green, Plate 000858/1 (W). Young—upper surface—Spinach Green, Plate 0960 (W), with a margin of Dark Red, Plate 5R3/7 (N); under surface—Spinach Green, Plate 0960/3 (W) with a suffusion of Dark Red, Plate 5R3/7 (N).

*Rachis (the supporting stem of the compound leaf).*—Medium. Upper side—grooved; with very small prickles. Under side—a few small prickles.

*Stipules.*—Moderately short; narrow; with short points turning out at an angle less than 45°.

Growth (in greenhouse):

*Habit.*—Upright; much-branched.

*Growth*—Moderately free.

*Canes.*—Medium diameter.

*Main stems.*—Color—Parsley Green, Plate 00962/3 (W), with some streaking of Moderate Brown, Plate 5YR3/3 (N). Thorns—few; from short to medium length; from straight to hooked slightly downward; narrow. Color—Moderate Yellowish-Brown, Plate 10YR4/4 (N). Prickles—none. Hairs—none.

*Branches.*—Color—Parsley Green, Plate 00962/2 (W). Thorns—few; from short to medium length; hooked slightly downward; with short, narrow base. Color—Dark Greenish-Yellow, Plate 7.5Y6/7 (N). Prickles — none. Hairs — none.

*New shoots.*—Color—moderate Yellow Green, Plate 2.5GY5/5 (N). Thorns—Few; from short to medium length; from straight to hooked slightly downward; with short narrow base. Color—Strong Brown, Plate 2.5YR4/7 (N) at base, shaded to Pale Orange Yellow, Plate 7.5YR9/4 (N) at tip. Prickles—none. Hairs—none.

*Reproductive organs*

Stamens: Medium number; arranged regularly about pistils; tucked in calyx.

Filaments: Medium length; most with anthers.

*Color.*—Varies from Dresden Yellow, Plate 64/3 (W) to Dresden Yellow, Plate 64/2 (W).

Anthers: Small; open at various times.

*Color.*—Sulphur Yellow, Plate 1.2 (W) with a Brownish-Orange, Plate 5YR5/8 (N) margin.

Pollen: Abundant.

*Color.*—Strong Orange, Plate 5YR7/11 (N).

Styles: Fairly even; short; thin and bunched.

*Color.*—Moderate Red, Plate 2.5R4/10 (N).

Pistils: Medium number.

Stigma: Color—strong Orange Yellow, Plate 10YR7/10 (N).

Ovaries: Some protruding from calyx.

Hips: Medium length; ovoid, but almost flat at top; with conspicuous neck; moderately smooth; walls thick and fleshy.

*Color (when seeds have developed but before pod ripens).*—Pod Green, Plate 061/2 (W).

Sepals: None observed; usually removed during hybridizing process.

Seeds: Many; medium size.

I claim:

A new and distinct variety of rose plant of the hybrid tea class, substantially as herein shown and described, characterized particularly as to novelty by the unique combination of a vigorous habit of growth, excellent flower productivity, distinctive and attractive white flowers of classic form which open from pointed buds, good color retention throughout the year when grown in greenhouses, and good tolerance to insecticides.

No references cited.

ANTONIO F. GUIDA, *Acting Primary Examiner.*